(12) United States Patent
Trayanova et al.

(10) Patent No.: US 10,531,922 B2
(45) Date of Patent: Jan. 14, 2020

(54) METHOD FOR COMPUTATIONALLY PREDICTING OPTIMAL PLACEMENT SITES FOR INTERNAL DEFIBRILLATORS IN PEDIATRIC AND CONGENITAL HEART DEFECT PATIENTS

(71) Applicant: THE JOHNS HOPKINS UNIVERSITY, Baltimore, MD (US)

(72) Inventors: Natalia Trayanova, Baltimore, MD (US); Lukas Rantner, Baltimore, MD (US); Fijoy Vadakkumpadan, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 377 days.

(21) Appl. No.: 14/889,544

(22) PCT Filed: Jun. 19, 2013

(86) PCT No.: PCT/US2013/046531
§ 371 (c)(1),
(2) Date: Nov. 6, 2015

(87) PCT Pub. No.: WO2014/182320
PCT Pub. Date: Nov. 13, 2014

(65) Prior Publication Data
US 2016/0113725 A1 Apr. 28, 2016

Related U.S. Application Data

(60) Provisional application No. 61/820,974, filed on May 8, 2013.

(51) Int. Cl.
*A61B 34/10* (2016.01)
*A61N 1/39* (2006.01)

(52) U.S. Cl.
CPC ............ *A61B 34/10* (2016.02); *A61N 1/3956* (2013.01); *A61B 2034/104* (2016.02); *A61B 2034/105* (2016.02)

(58) Field of Classification Search
CPC ............. G06F 19/3406; G06F 19/3437; A61B 5/04012; A61B 5/0402; A61B 5/046
See application file for complete search history.

(56) References Cited

U.S. PATENT DOCUMENTS

2005/0107834 A1 5/2005 Freeman et al.
2006/0161206 A1 7/2006 Efimov et al.
(Continued)

OTHER PUBLICATIONS

Jolley et al., "A computer modeling tool for comparing novel ICD electrode orientations in children and adults," 2008, Heart Rhythm, 5:565-572.*

(Continued)

*Primary Examiner* — Michael W Kahelin
(74) *Attorney, Agent, or Firm* — John Hopkins Technology Ventures

(57) ABSTRACT

The present invention includes a method for determining optimal placement sites for internal defibrillators in pediatric and congenital heart defect patients. The method is executed by creating a personalized active heart-torso model. The model is created using imaging scans (e.g., low resolution clinical scans) and advanced image processing techniques. The image processing results in a heart-torso mesh model. The ventricular portion of the mesh incorporates cell membrane dynamics. The combined torso-active ventricular defibrillation model can be used for patient specific modeling of the defibrillation process and optimal defibrillator placement can be determined. This method could also be used to decrease the energy needed for a defibrillation shock, because of the optimized defibrillator placement.

30 Claims, 6 Drawing Sheets

ANTERO-POSTERIOR VIEW

LEFT LATERAL VIEW

INFERO-SUPERIOR VIEW

(56) References Cited

U.S. PATENT DOCUMENTS

| | | |
|---|---|---|
| 2009/0234405 A1 | 9/2009 | Sommer et al. |
| 2009/0262109 A1* | 10/2009 | Markowitz .......... A61B 5/0422 345/419 |
| 2010/0211129 A1 | 8/2010 | Goedeke et al. |
| 2011/0224962 A1* | 9/2011 | Goldberger ......... G06F 19/3437 703/11 |
| 2011/0270338 A1 | 11/2011 | Cooke et al. |

OTHER PUBLICATIONS

Helm et al., "Ex vivo 3D diffusion tensor imaging and quantification of cardiac laminar structure," Oct. 2005, Magn Reson Med., 54(4):850-859.*

Helm et al., "Ex vivo 3D Diffusion Tensor Imaging and Quantification of Cardiac Laminar Structure," Oct. 2005, Magn Reson Med., 54(4):850-859. (Year: 2005).*

* cited by examiner

|  | TORSO | VENTRICLE |
|---|---|---|
| # NODES [MILLIONS] | 3.7 | 1.2 |
| # ELEMENTS [MILLIONS] | 4.3 | 1.4 |
| MEAN EDGE LENGTH [mm] | 1.5 | 0.5 |
*FIG. 1B*
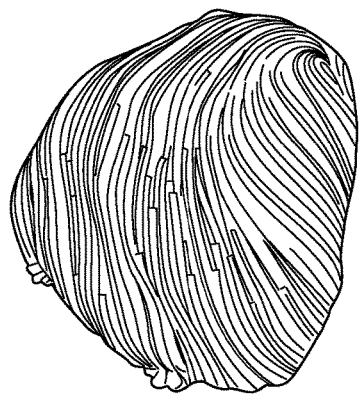
*FIG. 1A*
SHORT AXIS
$2 \times 2 \times 10$ mm$^3$
AXIAL
$1 \times 1 \times 6$ mm$^3$
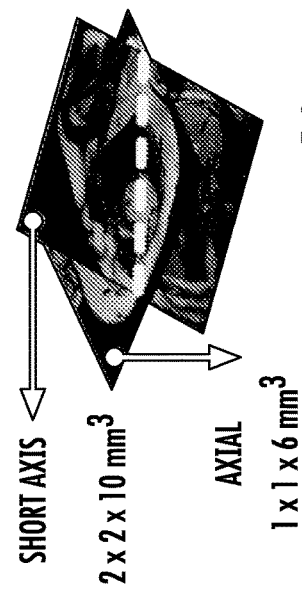
*FIG. 1C*

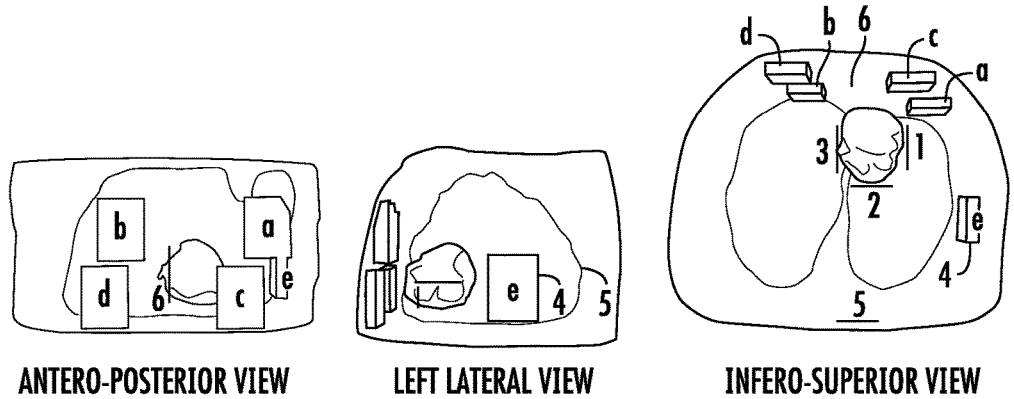

ANTERO-POSTERIOR VIEW    LEFT LATERAL VIEW    INFERO-SUPERIOR VIEW

FIG. 2A

| LEAD(S) | CAN | NOTES | NOTATION |
|---|---|---|---|
| LEFT EPICARDIAL (1) | RIGHT CHEST (D) | SINGLE EPI LEAD | LEpiL2RCC |
| POSTERIOR EPICARDIAL (2) | LEFT CHEST (C) | SINGLE EPI LEAD | PEpiL2LCC |
| RIGHT EPICARDIAL (3) | SUB-CLAVICULAR (A) | SINGLE EPI LEAD | REpiL2SCC |
| LEFT SUBCUTANEOUS (4) | RIGHT PARA-STERNAL (B) | SINGLE SQ LEAD | LSqL2RPSC |
| LEFT SUBCUTANEOUS (4) | RIGHT CHEST (D) | SINGLE SQ LEAD | LSqL2RCC |
| POSTERIOR SUBCUTANEOUS (5) | SUB-CLAVICULAR (A) | SINGLE SQ LEAD | PSqL2SCC |
| POSTERIOR SUBCUTANEOUS (5) | LEFT CHEST (C) | SINGLE SQ LEAD | PSqL2LCC |
| LEFT PARA-STERNAL (6) | SUB-AXILLARY (E) | SINGLE SQ LEAD | LPSL2SAC |
| LEFT SUBCUTANEOUS (4) POSTERIOR SUBCUTANEOUS (5), LEFT PARA-STERNAL (6) | SUB-CLAVICULAR (A) | MULTIPLE SQ LEADS | LSqLPSqLLPSL 2SCC |
| POSTERIOR SUBCUTANEOUS (5), LEFT PARA-STERNAL (6) | SUB-CLAVICULAR (A) | MULTIPLE SQ LEADS | PSqLLPSL2SCC |
| POSTERIOR SUBCUTANEOUS (5), LEFT PARA-STERNAL (6) | SUB-AXILLARY (E) | MULTIPLE SQ LEADS | PSqLLPSL2SAC |

METHOD FOR COMPUTATIONALLY PREDICTING OPTIMAL PLACEMENT SITES FOR INTERNAL DEFIBRILLATORS IN PEDIATRIC AND CONGENITAL HEART DEFECT PATIENTS

CROSS REFERENCE TO RELATED APPLICATIONS

This application is a 35 U.S.C. § 371 U.S. national entry of International Application PCT/US2013/046531, having an international filing date of Jun. 19, 2013, which claims the benefit of U.S. Provisional Application No. 61/820,974, filed May 8, 2013, the content of each of the aforementioned applications is herein incorporated by reference in their entirety.

GOVERNMENT SUPPORT

This invention was made with government support under grant number HL103428 awarded by the National Institutes of Health and grant number CDI1124804 awarded by the National Science Foundation. The government has certain rights in the invention.

FIELD OF THE INVENTION

The present invention relates generally to cardiology. More particularly the present invention relates to a computational model for determining placement of cardiac cardioverter/defibrillator devices.

BACKGROUND OF THE INVENTION

Defibrillation by strong electric shock is the only known procedure that reliably terminates ventricular fibrillation (VF). Implantable cardioverter-defibrillators (ICDs) have recently been implanted with increasing frequency in the pediatric population and in patients with congenital heart defects (CHD). In these patients, it is often not indicated or even impossible to implant a transvenous lead ICD because of the patient's small heart size and congenitally altered anatomy, thus non-standard ICD configurations have to be used. Such ICD configurations commonly involve individualized epicardial or subcutaneous lead placement. However, there is currently no reliable, personalized way of predicting which ICD configuration would have the lowest defibrillation threshold (DFT) and cardioversion threshold (CVT) in a patient. A low DFT is desirable because strong electric shocks damage cardiac myocytes, increase mortality, and can cause pain and psychological trauma. Thus, it is important to be able to predict the optimal ICD configuration for a specific patient (i.e., a configuration exhibiting a low DFT and CVT), especially in the case of a pediatric and/or CHD patient if a transvenous lead ICD configuration cannot be used.

It would therefore be advantageous to provide a method for computationally determining defibrillator lead and can placement in the heart.

SUMMARY

The foregoing needs are met, to a great extent, by the present invention, which includes a method for determining placement of a cardiac defibrillator in a subject that includes obtaining an image of the subject. The method also includes generating a three-dimensional image of the subject and labeling tissue regions within the three dimensional image of the subject. Additionally, the method includes generating a mesh for the three-dimensional image, incorporating active properties in the ventricular portion of the mesh, and simulating defibrillation with the combined torso-active ventricular defibrillation model utilizing the active properties in the ventricular portion of the mesh. The method also includes determining placement of the cardiac defibrillator in the subject.

In accordance with an aspect of the present invention the image can take the form of a magnetic resonance image. The method further includes assigning fiber and sheet orientations to a ventricular model. Also, the method includes building a binary image of ventricular geometry. The image of the subject can take the form of at least one of a torso image and a cine image or other image of the subject's heart or a combination thereof. Further, the method includes eliminating breathing motion errors. Epi- and endocardial contours can be drawn in to the model. An octree-based algorithm can be used to produce the mesh. An area of interest can be added to the mesh. The area of interest can take the form of a ventricular region. The method can base current flow in cardiac tissue in the defibrillation model on bidomain and monodomain representations. Defibrillation outcomes for predetermined cardiac defibrillator placement on the model can be recorded and can also be recorded for cardioversion shocks at predetermined cardiac defibrillator placements on the model. The method can also include choosing the cardiac defibrillator placement with a lowest defibrillation threshold and/or lowest cardioversion threshold or, otherwise, choosing a cardiac defibrillator placement with a comparatively low defibrillation and/or cardioversion threshold that is otherwise deemed favorable by the responsible health care provider or providers over the defibrillator placement with the lowest defibrillation and/or cardioversion threshold.

In accordance with another aspect of the present invention, a fixed computer readable medium can be programmed to execute a method including obtaining an image of the subject. The method also includes generating a three-dimensional image of the subject and labeling tissue regions within the three dimensional image of the subject. Additionally, the method includes generating a mesh for the three-dimensional image, incorporating active properties in the ventricular portion of the mesh, and simulating defibrillation with the combined torso-active ventricular defibrillation model utilizing the active properties of the ventricular portion of the mesh. The method also includes determining placement of the cardiac defibrillator in the subject.

In accordance with another aspect of the present invention, a method for determining placement of cardiac defibrillator leads in a subject includes obtaining an image of the subject and generating a three-dimensional image of the subject. The method includes labeling tissue regions within the three dimensional image of the subject and generating a mesh for the three-dimensional image to form a defibrillation model. The method also includes simulating defibrillation with the defibrillation model and determining placement of the cardiac defibrillator in the subject. This method can also be executed using a fixed computer readable medium.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIG. 1A illustrates axial torso scans and short-axis cine scans of a subject.

FIG. 1B illustrates a table listing the number of nodes, number of elements, and mean edge length of a resulting mesh, and of a ventricular portion of the mesh, wherein the mesh is created using the axial torso scans and short-axis cine scans of FIG. 1A.

FIG. 1C illustrates a streamlined image of the fiber orientations in the ventricular mesh.

FIG. 2A illustrates a diagram of an exemplary heart-torso mesh with exemplary ICD can and ICD lead placement locations.

FIG. 2B illustrates a table of 11 ICD configurations tested with respect to the example described herein.

DETAILED DESCRIPTION OF THE PREFERRED EMBODIMENTS

Figure 3:
FIG. 3 illustrates sample clinically observed echocardiogram traces and simulated ECG panel traces of an exemplary pediatric CHD patient with tricuspid valve atresia.
Figure 4A:
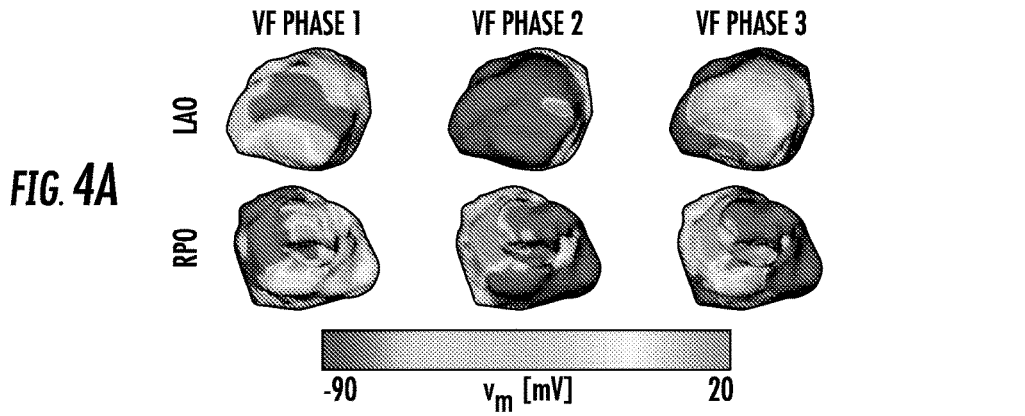
FIG. 4A illustrates left anterior oblique (LAO; top row) and right posterior oblique (RPO; bottom row) $V_m$ maps of the three VF phases to which defibrillation shocks were applied.
Figure 4B:
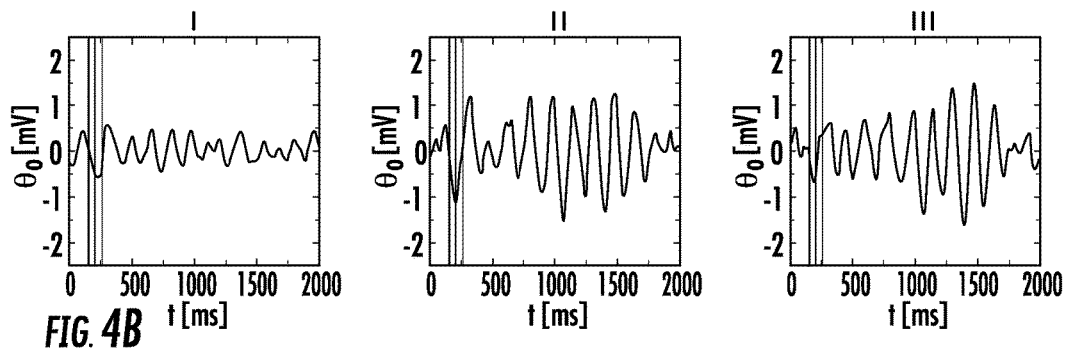
FIG. 4B illustrates limb lead ECG traces of VF. Red lines mark the three VF phases from panel A.
Figure 4C:
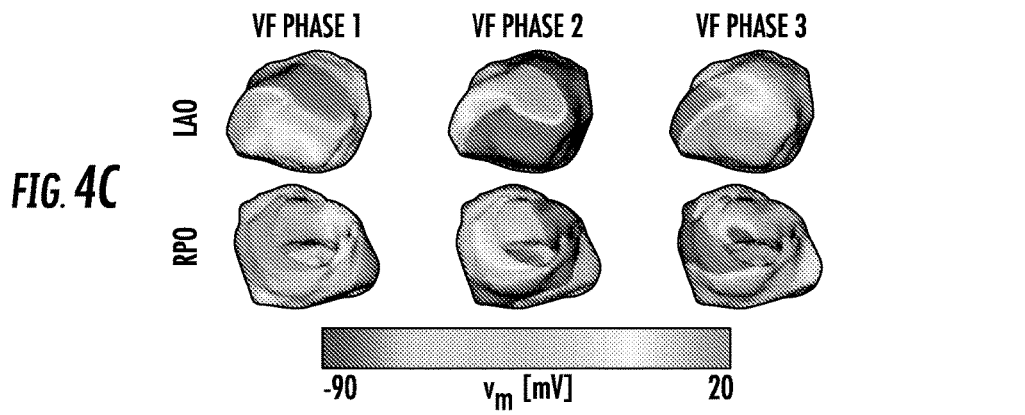
FIG. 4C illustrates LAO and RPO $V_m$ maps of the three VT phases to which cardioversion shocks were applied.
Figure 4D:
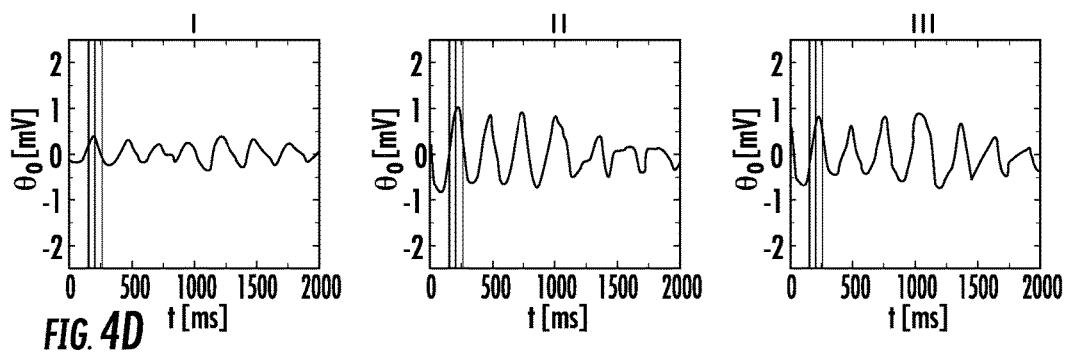
FIG. 4D illustrates limb lead ECG traces of VT. Red lines mark the three VT phases from panel C.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention includes a method for determining patient-specific electrically optimal placement sites for internal defibrillators in pediatric and congenital heart disease patients. The method preferably is executed by creating a personalized active heart-torso model with realistic ventricular fiber architecture. The model is created using imaging can (for example, low-resolution clinical images) and advanced image processing techniques. The image processing results in a ventricular model to which fiber and sheet orientations are assigned, imbedded in a torso model with the different torso regions delineated (lungs, fat, skeletal muscle, etc.). Therefore, the combined heart-torso model can be used for patient specific modeling of the optimal defibrillation configuration for the given patient. This method could also be used to decrease the energy needed for a defibrillation shock, because of the optimized defibrillator placement.

More particularly, clinical images, such as magnetic resonance (MR) images of the subject are obtained. MR images are currently preferable because MR acquisition minimizes the subject's exposure to radiation. However, any suitable imaging modality known to or conceivable by one of skill in the art could also be used. Therefore, high resolution images can also be used in the implementation of the method. For the present method, preferably axial torso images and short axis (SA) cine images of the subject's heart can be used. Other suitable images could also be used and the axial torso and short axis cine images example should not be considered limiting. In each slice in the axial torso image, tissue regions are manually labeled, creating several sets of binary image slices, each set corresponding to one tissue type. However, tissue regions can also be labeled using a computer or other suitable modality. Each set of image slices is then interpolated into 1 mm isotropic resolution using the variational implicit functions method, and the interpolated data merged to form one image; other suitable interpolation techniques could also be used. By labeling the above tissue types, a segmented three-dimensional (3D) image of the torso labeled with tissue types is generated. The described segmentation, labeling, and interpolation methods represent an example and any suitable image processing approach known to or conceivable by one of skill in the art could also be used.

From the low resolution short axis (SA) cine image of the patient heart, a binary image of the ventricular geometry in diastole is built at 1 mm isotropic voxel size. While 1 mm isotropic voxel size is provided as an example, any suitable voxel size determined by one of skill in the art could also be used. In this process, the breathing motion errors in the SA data are first eliminated based on horizontal and vertical long axis (LA) scans. Epi- and endocardial contours are manually drawn on the motion-corrected SA slices, with papillary muscles included as part of the ventricular wall. This could also be executed using a computer or other suitable modality. The contours are interpolated to create a 1 mm isotropic 3D image of the ventricular geometry with separate labels for ventricular tissue and blood. While a 1 mm isotropic 3D image is used as an example, any suitable image size determined by one of skill in the art could also be used. This image is then merged with the segmented image of the torso by means of coordinate transformations calculated from acquired image header data, to create the final image of the torso and heart, labeled with different tissue types. The present method is designed to utilize modalities such as cine MRI that are optimized to image the heart specifically. If separate image data for the heart are not available, the methods presented here can still be implemented, by labeling the heart geometry directly in the torso image. The described segmentation, labeling, interpolation, and merging methods represent an example and any suitable image processing approach known to or conceivable by one of skill in the art could also be used. An unstructured mesh was generated from the final image using a methodology employing an efficient octree-based algorithm to produce boundary-fitted, locally refined, smooth conformal meshes directly from segmented images. The ventricular region of the mesh is locally refined, and the rest of the torso coarsened, to reduce the mesh size without compromising important geometric detail. Fiber and sheet orientations are assigned to the ventricular elements using a validated rule-based technique. The described model generation methods represent an example and any suitable image processing and mesh generation approaches known to or conceivable by one of skill in the art could also be used.

The finite element mesh constructed with the above pipeline is parameterized to construct a human heart-torso defibrillation model with an active, multi-scale model of the heart. The resultant model is referred to as a torso-active ventricular defibrillation model. The torso-active ventricular defibrillation model exhibits cardiac electrophysiological activity over a predetermined period of time. The torso-active ventricular defibrillation model can also be used to demonstrate cardiac activity from the molecular level to the system level and incorporates cell membrane dynamics. Additionally, the torso-active ventricular defibrillation model incorporates active properties in the ventricular portion of the mesh, and simulates defibrillation. The mathematical description of current flow in cardiac tissue is based on the bidomain and monodomain representations. The described cardiac tissue description represents an example and any other approach for cardiac tissue description known to or conceivable by one of skill in the art could also be used. While an active model is described herein as the preferable method, other modeling methodologies could also be used, such as passive cardiac modeling. The active model described herein can also be optimized for use with respect to other cardiac anatomy, not just the ventricular region. The ventricular defibrillation model is used here by way of example.

Several ICD configurations are tested using various locations if the ICD can and of the ICD lead (or leads in the case of configurations with multiple leads). From the chosen ICD can and lead locations, ICD configurations are assembled so that the shock vector would be across the ventricles for each configuration, and so that configurations with epicardial leads and with single and multiple subcutaneous leads can be tested. Other choices of shock vector can also be used. VT and VF are induced and defibrillation shocks are then delivered to the constructed human heart-torso model, which incorporated the ionic processes in ventricular myocytes. In order to ensure shock delivery during different "phases" of VF and VT, different instants (or phases) during VF and during VT—i.e., different pre-shock transmembrane potential ($V_m$) distributions in the ventricles staring VT and VF—can be used to apply shocks to, for example. Exponentially truncated, monophasic or biphasic defibrillation or cardioversion shocks are applied from the ICD leads of the various ICD configurations; other shock waveforms can also be used. A DFT grid—a two-dimensional grid representing defibrillation outcomes for the ICD configurations—for the VF instants, and for a range of shock strengths, is assembled for shocks applied to the fibrillating heart, and a cardioversion threshold (CVT) grid—an analogue to the DFT grid, but representing the outcomes of VT cardiaversion shocks—is constructed for shocks applied during VT. The DFT and CVT were defined as the lowest energy shocks that terminate the arrhythmia for all VF and VT phases, respectively. The electrically optimal ICD configuration is determined by having the lowest DFT and CVT in the DFT and CVT grids. The described defibrillation and cardioversion simulation-testing methods represent an example and any suitable defibrillation and any cardioversion threshold testing approach known to or conceivable by one of skill in the art could also be used. For example, only defibrillation simulation-testing could be used.

The present method can be executed using a computing device and a fixed computer readable medium programmed to execute steps of the method. The computing device can take the form of a computer, tablet, smartphone, server, or other computing device known to or conceivable to one of skill in the art. The computing device can be hard wired or wirelessly networked to a source for the images, such as an imaging device, a server holding image data, a second computing device, or other device for storage of image data, known to or conceivable by one of skill in the art. The fixed computer readable medium can take the form of a floppy disk, cd-ROM, DVD, hard drive, server, or any other suitable computer readable medium known to or conceivable by one of skill in the art.

Example

An exemplary implementation of the present invention is described herein, in order to further illustrate the present invention. The exemplary implementation is included merely as an example and is not meant to be considered limiting. Any implementation of the present invention on any suitable subject known to or conceivable by one of skill in the art could also be used, and is considered within the scope of this application.

Data Acquisition

A clinical MRI (1.5 T) dataset acquired from a 14-year-old male pediatric patient with tricuspid valve atresia is used throughout this example. Because of the tricuspid valve atresia, the right ventricle (RV) was not recognizable on the clinical low-resolution MRI images. This dataset included axial torso scans, and short-axis (SA) and long-axis (LA) cardiac cine scans. The axial image (27 slices, 384×300 pixels each) had a resolution of 1×1×6 mm³, and the SA cine scans (11 slices, 144×192 pixels each) had a resolution of 2×2×10 mm³, as illustrated in FIG. 1A.

Image Processing Pipeline for Heart-Torso Model Construction from Clinical MRI Data A pipeline is used for constructing smooth and locally refined active heart-torso models with ventricular fiber architecture from low-resolution clinical MRI scans, using advanced image processing techniques. The heart-torso model of the pediatric patient with tricuspid valve atresia was used as an example. It should be noted that the methodology described here can be applied to any clinical MRI dataset of similar (or higher) resolution. As described above, in each slice in the axial torso image (27 slices in this dataset), tissue regions (6 regions here: lungs, fat, bones, blood, muscles, torso outline) were manually labeled, creating several sets of binary image slices, each set corresponding to one tissue type. Each set was then interpolated into 1 mm isotropic resolution using it variational implicit functions method, and the interpolated data merged to form one image. The outer three pixels of the torso outline were then labeled as skin, and the remainder of the torso outline tissue type was labeled as conductive medium. By labeling the above tissue types, a segmented three-dimensional (3D) image of the torso labeled with tissue types (7 tissue types here, not yet including the heart) was generated. This labeled 3D image had a significantly smaller voxel size than the acquired clinical MRI image, as interpolation estimated a large amount of missing data.

From the low-resolution SA cine image of the patient heart, a binary image of the ventricular geometry in diastole was built at 1 mm isotropic voxel size (only left ventricle in this patient as there was no recognizable RV). In this process, the breathing motion errors in the SA data were first eliminated based on horizontal and vertical LA scans, as described elsewhere. Epi- and endocardial contours were manually drawn on the motion-corrected SA slices, with papillary muscles included as part of the ventricular wall. The contours were interpolated to create a 1 mm isotropic 3D image of the ventricular geometry with separate labels for ventricular tissue and blood. This image was then merged with the segmented image of the torso by means of coordinate transformations calculated from acquired image header data to create the final image of the torso and heart, labeled with different tissue types (8 tissue types here).

An unstructured mesh was automatically generated from the final image. This methodology employs an efficient octree-based algorithm to produce boundary-fitted, locally refined, smooth conformal meshes directly from segmented images. The ventricular region of the mesh was locally refined, and the rest of the torso coarsened, to reduce the mesh size without compromising important geometric detail. The mean edge length, number of nodes, and number of elements of the tricuspid valve atresia heart-torso mesh are listed in FIG. 1B. Fiber and sheet orientations are assigned to the ventricular elements using a recently developed and validated rule-based technique. FIG. 1C presents a streamlined visualization of the fiber orientations.

Model Formulation and Parameters

The finite element mesh constructed with the above pipeline is parameterized as described below to construct the first human heart-torso defibrillation model with an active, multi-scale model of the heart.

The mathematical description of current flow in cardiac tissue was based on the bidomain and monodomain representations. The bidomain formulation was used when shocks were applied, and for the computation of the electrocardiogram (ECG), whereas the computationally less demanding monodomain formulation was used to simulate propagation in the absence of externally applied electric fields. The bidomain and monodomain equations were solved here with the Cardiac Arrhythmia Research Package (CARP), but any other suitable representation of cardiac electrical behavior of solver software could also be used. Ionic properties of cardiac myocytes were modeled with the ten Tusscher model of the human ventricular myocyte. Realistic apico-basal and transmural electrophysiological heterogeneities were incorporated into the model, and longitudinal, transverse, and sheet-normal conductivities were chosen to achieve realistic propagation patterns.

In order to preserve the same conduction velocities (CVs) and propagation patterns between the monodomain and bidomain simulations, we used bulk conductivity ($g_{bulk}$) as the monodomain conductivity with $$g_{bulk,\zeta} = \frac{g_{i,\zeta} g_{e,\zeta}}{g_{i,\zeta} + g_{e,\zeta}},$$

where $g_i$ is the bidomain intracellular conductivity and $g_e$ the bidomain extracellular conductivity, and $\zeta$ represents longitudinal, transverse, or sheet-normal fiber direction.

Ionic properties of cardiac myocytes were modeled with the ten Tusscher model of the human ventricular myocyte. A 40% apico-basal gradient in the maximal conductance of the slowly activating component of the delayed rectifier current ($I_{Ks}$) was implemented. The ventricular wall was divided equally into endocardial, midmyocardial, and epicardial cell layers, and the maximum conductances of the transient outward ($I_{to}$) and $I_{Ks}$ potassium channels were adjusted to represent realistic transmural electrophysiological heterogeneity. In order to make the simulated action potential duration (APD) similar to the QT interval of the patient's ECG, as illustrated in FIG. 3, $G_{Ks}$ was increased, decreasing APD.

Implantable Cardioverter-Defibrillator Placement

Due to the tricuspid valve atresia, there was no transvenous access to the RV and, thus, placement of a transvenous lead ICD was not possible. Hence, a non-standard ICD configuration had to be used. Several ICD configurations were tested using various locations of the ICD can and of the ICD lead (or leads in the case of configurations with multiple leads). Five realistic placement options for the ICD can were identified. Two of these ICD can locations were on the upper chest, two on the lower chest, and one was a sub-axillary location, as illustrated in FIG. 2. The dimensions of the ICD can were 6×5×1.5 cm$^3$, roughly the size of most ICD cans used today. Next, six locations for the placement of the ICD lead were identified, three on the epicardium, and three subcutaneous, as illustrated in FIG. 2. The choice of lead placement options enabled the exploration of both epicardial and subcutaneous lead locations and multiple electric field vectors. ICD lead dimensions were 5×0.2×0.2 cm$^3$, roughly the size of the RV coil of a typical transvenous ICD lead, as this type of lead is commonly used "off-label" for non-transvenous lead placement in the pediatric and CHD populations. From the chosen ICD can and lead locations, 11 ICD configurations were assembled so that the shock vector would be across the ventricles for each configuration, and so that configurations with epicardial leads and with single and multiple subcutaneous leads could be tested. Thus, each ICD configuration consisted of one ICD can and between one and three ICD leads. Three of the 11 ICD configurations had epicardial leads, five had single subcutaneous leads, and three configurations had multiple subcutaneous leads, as illustrated in FIG. 2.

Study Protocol

Because the heart model lacked a representation of the atria, the P wave was absent from the simulated ECGs. Sinus rhythm was simulated by using a cable-based representation of the Purkinje system, where Purkinje activation in response to His bundle stimulation was simulated and junctional activation times were used as pacing timing offsets for sinus rhythm simulation.

Defibrillation shocks were delivered to the constructed human heart-torso model, which incorporated the ionic processes in ventricular myocytes. In order to ensure shock delivery during different "phases" of VF and VT, three different instants (or phases) during VF and three different instants during VT—i.e., different pre-shock $V_m$ distributions in the ventricles during VT and VF—were chosen to apply electric shocks to. Exponentially truncated, biphasic defibrillation or cardioversion shocks of 7 ms duration (3.5 ms duration and 50% tilt in each phase, positive polarity in first phase) were applied from the ICD leads of the 11 ICD configurations, with the ICD can used as ground. A DFT grid—a two-dimensional grid representing defibrillation outcomes for the 11 ICD configurations—for the three VF instants, and for a range of shock strengths, was assembled for shocks applied to the fibrillating heart, and a cardioversion threshold (CVT) grid—an analogue to the DFT grid, but representing the outcomes of VT cardioversion shocks—was constructed for shocks applied during VT. The DFT and CVT were defined as the lowest energy shocks that terminated the arrhythmia for all VF and VT phases, respectively. Arrhythmia was considered terminated if no propagation was present 1 s after shock onset.

The rationale for constructing both a DFT and a CVT grid to be used in choosing the optimal ICD configuration in the pediatric CHD patient was as follows: To prevent sudden cardiac death, an ICD must be capable of terminating VF. An ICD also needs to be able to terminate VT, as cardioversion by electric shock might have to be applied if anti-tachycardia pacing (ATP) fails or if ATP is not possible due to the absence of a pace-sense lead in certain ICD configurations. The occurrence of VT in CHD patterns, specifically in patients with repaired tetralogy of Fallot, is well-documented. ICD configurations that led to both low DFT and low CVT were considered favorable here.

Results

Heart-Torso Model and Electrocardiogram

The tricuspid valve atresia heart-torso model is presented in FIG. 2; different tissue regions throughout the torso are clearly visible (shown are ventricle, bones, lungs, and skin; not shown in FIG. 2: blood, muscles, fat, remaining conductive medium). Select clinically recorded ECG traces from the tricuspid valve atresia patient as well as simulated ECGs are shown in FIG. 3. The simulated ECG traces match the clinical recordings very well, especially for the limb leads and augmented limb leads, showing that the heart-torso model is an appropriate representation of the patient's overall electrophysiology.

Defibrillation and Cardioversion Thresholds

Figure 5:
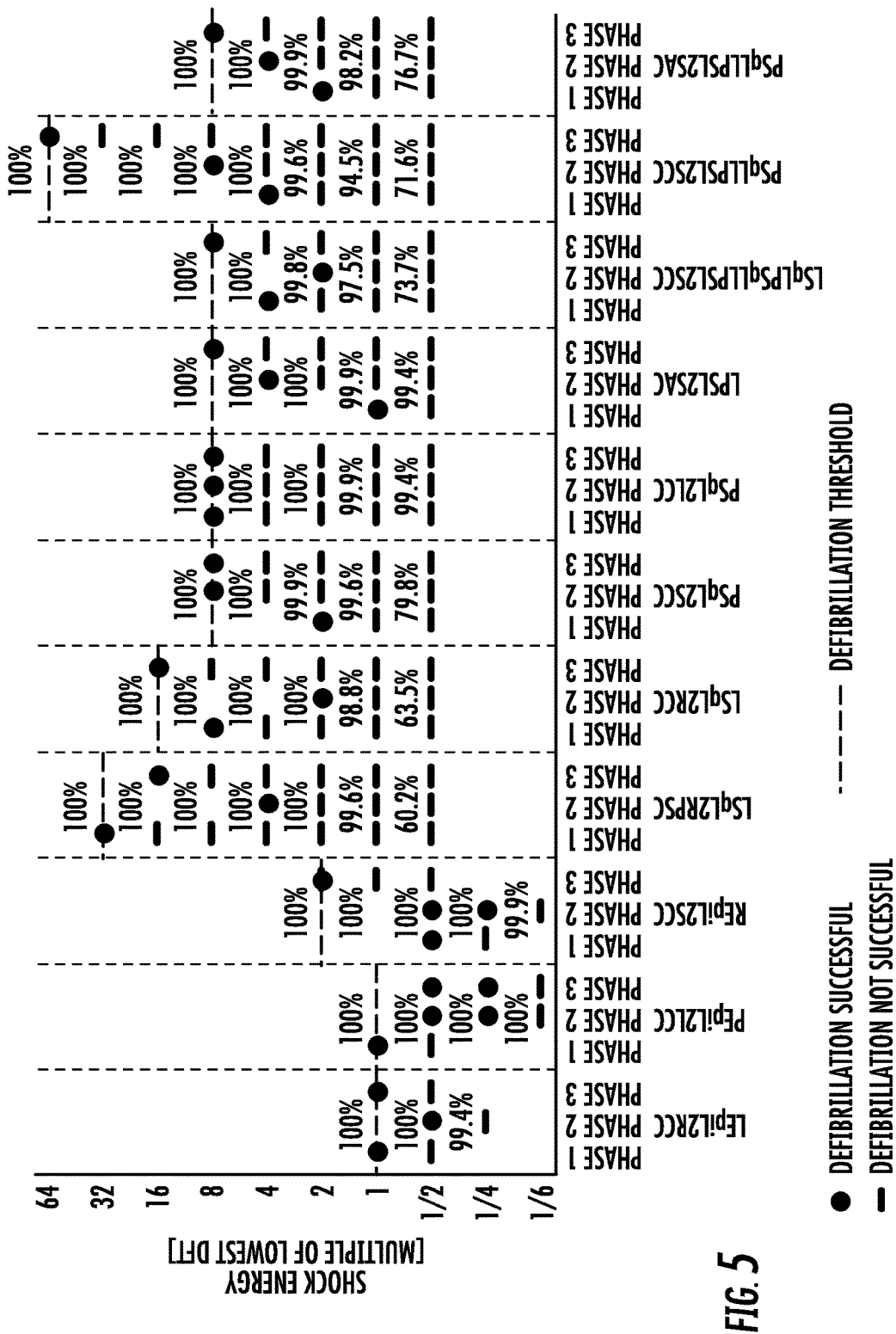
FIG. 5 illustrates DFTs for the 11 tested ICD configurations.

FIGS. 4A-4D show $V_m$ maps of the three VF and three VT pre-shock phases, along with 2 s excerpts of limb lead ECG recordings during VF and VT. FIG. 5 presents the DFT grid for the 11 ICD configurations. DFTs were lowest for ICD configurations with an epicardial lead. Even the lowest DFT among ICD configurations with subcutaneous leads was four times the highest DFT for configurations with an epicardial lead. There was a four-fold difference between the highest and lowest DFTs among ICD configurations with a single subcutaneous lead. There was an eight-fold difference between the highest and lowest DFTs among ICD configurations with multiple subcutaneous leads. The highest DFT among all 11 ICD configurations was 64 times the lowest DFT.

Figure 6:
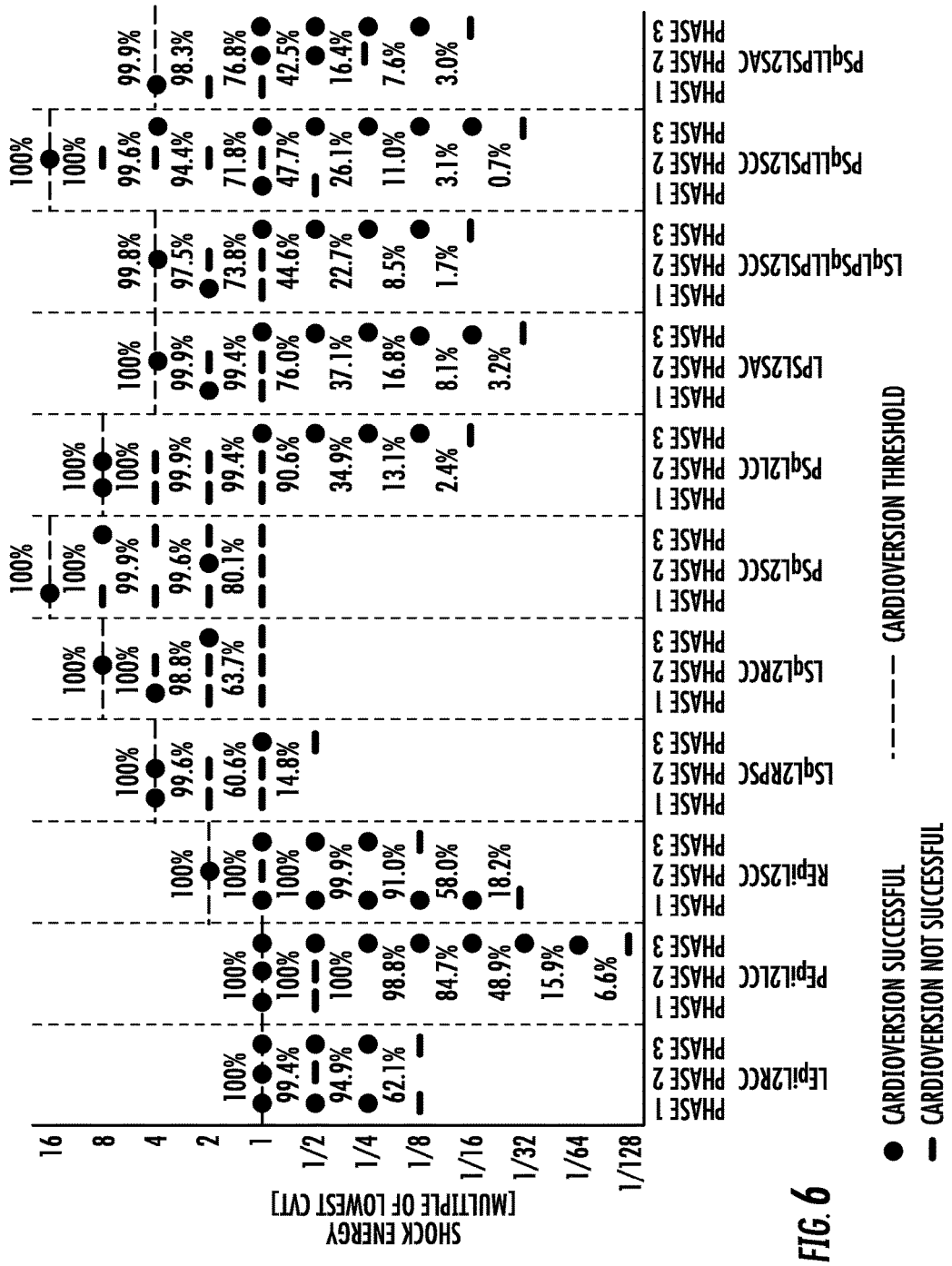
FIG. 6 illustrates CVTs for the 11 tested ICD configurations.

FIG. 6 shows the CVT grid. Not only DFTs, but also CVTs were lowest for ICD configurations with epicardial leads. The lowest CVT for ICD configurations with subcutaneous leads was twice the highest CVT among any configuration with an epicardial lead. There was a four-fold difference between the highest and lowest CVTs among single subcutaneous lead ICD configurations. Likewise, the highest CVT of an ICD configuration with multiple subcutaneous leads was four times the lowest CVT among multiple subcutaneous lead configurations. Of all 11 ICD configurations, there was a 16-fold difference between the highest and lowest CVTs.

The ICD configuration with a left epicardial lead and a right chest can (LEpiL2RCC in FIGS. 5, 6) as well as the configuration with a posterior epicardial lead and a left chest can (PEpiL2LCC in FIGS. 5, 6) had both the lowest DFT and CVT overall. Among the configurations with a single subcutaneous lead, a left para-sternal lead and sub-axillary can (LPSL2SAC in FIGS. 5, 6) resulted in the lowest DFT and CVT. The same DFT and CVT was shared by two configurations with multiple subcutaneous leads: the ICD configuration with a left subcutaneous lead, a posterior subcutaneous lead, a left para-sternal lead, and a sub-clavicular can (LSqLPSqLLPSL2SCC in FIGS. 5, 6); and the configuration with a posterior subcutaneous lead, a left para-sternal lead, and a sub-clavicular can (PSqLLPSL2SCC in FIGS. 5, 6).

Although the present invention has been described in connection with preferred embodiments thereof, it will be appreciated by those skilled in the art that additions, deletions, modifications, and substitutions not specifically described may be made without departing from the spirit and scope of the invention as defined in the appended claims. It should be noted that while the present invention is described with respect to cardiac lead placement for defibrillation in pediatric patients this method could potentially be applied to adults as well as to other applications of cardiac stimulation other than defibrillation.

The invention claimed is:

1. A method for determining placement of a cardiac defibrillator in a subject comprising:
   obtaining an image of the subject;
   generating a three-dimensional image of the subject from the image of the subject;
   labeling tissue regions within the three dimensional image of the subject;
   generating a mesh for the three-dimensional image;
   incorporating active properties in a ventricular portion of the mesh, wherein the ventricular portion of the mesh comprises ventricular fiber architecture;
   creating a personalized active heart-torso model for the subject with realistic ventricular fiber architecture which exhibits cardiac electrophysiological activity over a predetermined period of time;
   simulating a number of defibrillation events with a combined torso-active ventricular defibrillation model that utilizes the active properties of the ventricular portion of the mesh;
   creating a defibrillation threshold and cardioversion threshold grid from the simulation of the defibrillation events; and
   determining placement of the cardiac defibrillator in the subject based on simulating the number of defibrillation events.

2. The method of claim 1 further comprising using a magnetic resonance image as the image of the subject.

3. The method of claim 1 further comprising assigning fiber and sheet orientations to the ventricular portion of the mesh.

4. The method of claim 3 further comprising building a binary image of ventricular geometry.

5. The method of claim 1 further comprising obtaining the image of the subject wherein the image of the subject takes the form of at least one of a torso image and a cine image or other image of the subject's heart or a combination thereof.

6. The method of claim 1 further comprising eliminating breathing motion errors.

7. The method of claim 1 further comprising drawing in epi- and endocardial contours.

8. The method of claim 1 further comprising using an octree-based algorithm to produce the mesh.

9. The method of claim 1 further comprising locally refining an area of interest of the mesh.

10. The method of claim 9 further comprising locally refining the area of interest wherein the area of interest takes the form of a ventricular region.

11. The method of claim 1 further comprising mapping current flow in cardiac tissue in the ventricular portion of the mesh on bidomain and monodomain representations.

12. The method of claim 1 further comprising recording simulated defibrillation outcomes for predetermined cardiac defibrillator placement on the model.

13. The method of claim 12 further comprising recording simulated defibrillation outcomes for cardioversion shocks at predetermined cardiac defibrillator placements on the model.

14. The method of claim 13 further comprising choosing a cardiac defibrillator placement with a lowest defibrillation threshold and/or lowest cardioversion threshold or, otherwise, choosing a cardiac defibrillator placement with a comparatively low defibrillation and/or cardioversion threshold that is otherwise deemed favorable by the responsible health care provider or providers over the defibrillator placement with the lowest defibrillation and/or cardioversion threshold.

15. A non-transitory computer readable medium programmed to execute a method comprising:
    obtaining an image of the subject;
    generating a three-dimensional image of the subject from the image of the subject;
    labeling tissue regions within the three dimensional image of the subject;
    generating a mesh for the three-dimensional image;
    incorporating active properties in a ventricular portion of the mesh, wherein the ventricular portion of the mesh comprises ventricular fiber architecture;
    creating a personalized active heart-torso model for the subject with realistic ventricular fiber architecture which exhibits cardiac electrophysiological activity over a predetermined period of time;
    simulating a number of defibrillation events with a combined torso-active ventricular defibrillation model that utilizes the active properties of the ventricular portion of the mesh;
    creating a defibrillation threshold and cardioversion threshold grid from the simulation of the defibrillation events; and
    determining placement of the cardiac defibrillator in the subject based on simulating the number of defibrillation events.

16. The fixed computer readable medium of claim 15 wherein the image comprises a magnetic resonance image.

17. The fixed computer readable medium of claim 15 further comprising being programmed for assigning fiber and sheet orientations to the ventricular portions of the mesh.

18. The fixed computer readable medium of claim 17 further comprising being programmed for building a binary image of ventricular geometry.

19. The fixed computer readable medium of claim 15 wherein the image of the subject comprises at least one of a torso image and a cine image or other image of the subject's heart, or a combination thereof.

20. The fixed computer readable medium of claim 15 further comprising being programmed for eliminating breathing motion errors.

21. The fixed computer readable medium of claim 15 further comprising being programmed for drawing in epi- and endocardial contours.

22. The fixed computer readable medium of claim 15 further comprising being programmed for using an octree-based algorithm to produce the mesh.

23. The fixed computer readable medium of claim 15 further comprising being programmed for locally refining an area of interest of the mesh.

24. The fixed computer readable medium of claim 23 further comprising being programmed for the area of interest being a ventricular region.

25. The fixed computer readable medium of claim 15 further comprising being programmed for mapping current flow in cardiac tissue in the defibrillation model on bidomain and monodomain representations.

26. The fixed computer readable medium of claim 15 further comprising being programmed for recording defibrillation outcomes for predetermined cardiac defibrillator placement on the model.

27. The fixed computer readable medium of claim 26 further comprising being programmed for recording outcomes for cardioversion shocks at predetermined cardiac defibrillator placements on the model.

28. The fixed computer readable medium of claim 27 further comprising being programmed for choosing the cardiac defibrillator placement with a lowest defibrillation threshold and/or lowest cardioversion threshold or, otherwise, choosing a cardiac defibrillator placement with a comparatively low defibrillation and/or cardioversion threshold that is otherwise deemed favorable by the responsible health care provider or providers over the defibrillator placement with the lowest defibrillation and/or cardioversion threshold.

29. A method for determining placement of cardiac defibrillator leads in a subject comprising:
    obtaining an image of the subject;
    generating a three-dimensional image of the subject based on the image of the subject;
    labeling tissue regions within the three dimensional image of the subject;
    generating a mesh for the three-dimensional image to form a defibrillation model;
    simulating automatically a number of defibrillation events with the defibrillation model, wherein a ventricular portion of the mesh comprises ventricular fiber architecture;
    creating a personalized active heart-torso model for the subject with realistic ventricular fiber architecture which exhibits cardiac electrophysiological activity over a predetermined period of time;
    creating a defibrillation threshold and cardioversion threshold grid from the simulation of the defibrillation events; and
    determining placement of the cardiac defibrillator in the subject based on simulating the number of defibrillation events.

30. A non-transitory computer readable medium programmed to execute a method comprising:
    obtaining an image of the subject;
    generating a three-dimensional image of the subject from the image of the subject;
    labeling tissue regions within the three dimensional image of the subject;
    generating a mesh for the three-dimensional image to form a defibrillation model;
    simulating a number of defibrillation events with the defibrillation model, wherein a ventricular portion of the mesh comprises ventricular fiber architecture;
    creating a personalized active heart-torso model for the subject with realistic ventricular fiber architecture which exhibits cardiac electrophysiological activity over a predetermined period of time;
    creating a defibrillation threshold and cardioversion threshold grid from the simulation of the defibrillation events; and determining placement of the cardiac defibrillator in the subject based on simulating the number of defibrillation events.

\* \* \* \* \*